US006387916B1

(12) United States Patent
Mayer et al.

(10) Patent No.: US 6,387,916 B1
(45) Date of Patent: May 14, 2002

(54) ANTI-INFLAMMATORY USES OF MANZAMINES

(75) Inventors: Alejandro Mayer, Naperville, IL (US); Sarath P. Gunasekera, Vero Beach, FL (US); Shirley A. Pomponi, Fort Pierce, FL (US); Susan H. Sennett, Sebastian, FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 0 days.

(21) Appl. No.: 09/535,291

(22) Filed: Mar. 24, 2000

Related U.S. Application Data

(60) Provisional application No. 60/125,903, filed on Mar. 24, 1999, and provisional application No. 60/164,294, filed on Nov. 8, 1999.

(51) Int. Cl.[7] .............................................. A01N 43/42
(52) U.S. Cl. ....................... 514/281; 514/292; 514/321; 514/322
(58) Field of Search ................................ 514/321, 322, 514/281, 292

(56) References Cited

U.S. PATENT DOCUMENTS

| 4,895,852 A | 1/1990 | Higa et al. ................... 514/281 |
| 4,895,853 A | 1/1990 | Higa et al. ................... 514/281 |
| 4,895,854 A | 1/1990 | Higa et al. ................... 514/281 |
| 5,859,006 A | 1/1999 | Daugan ....................... 514/245 |

FOREIGN PATENT DOCUMENTS

| WO | 9743287 | 5/1997 |
| WO | 9959592 | 5/1999 |

OTHER PUBLICATIONS

Ichiba, Toshio, May M. Corgiat, Paul J. Scheuer (Jan. 1994) "8–Hydroxymanzamine A, A β–Carboline Alkaloid From A Sponge, *Pachypellina* Sp." *Journal of Natural Products* 57(1):168–170.

Kondo, K. et al. (Feb. 21, 1994) "Structures of ircinals A and B, novel alkaloids from the Okinawan marine sponge *Ircinia* sp." Chemical Abstracts vol. 120(8), p. 636, abstract No. 86212b.

Dray, Andy (1992) "Neuropharmacological Mechanisms Of Capsaicin and Related substances" *Biochemical Pharmacology* 44(4):611–615.

Faden, Alan I. and Steven Salzman (1992) "Pharmacological strategies in CNS trauma" *TIPS* 13:29–35.

Gillman, A.G. et al. eds (1980) The Pharmacological Basis of Therapeutics, ppg. 697–713, 1482, and 1489–1491.

Mallat, M. and B. Chamak (1994) Brain macrophages: neurotoxic or neurotrophic effector cells? *Journal of Leukocyte Biology* 56:416–422.

Mayer, Alejandro M.S., Keith B. Glaser, Robert S. Jacobs (1988) "Regulation of Eicosanoid Biosynthesis in Vitro and in Vivo by the Marine Natural Product Manoalide: A Potent Inactivator of Venom Phospholipases" *The Journal of Pharmacology and Experimental Therapeutics* 244(3):871–878.

Mayer, Alejandro M.S. (1998) "Therapeutic Implications Of Microglia Activation By Lipopolysaccharide And Reactive Oxygen Species Generation In Septic Shock And Central Nervous System Pathologies: A Review" *Medicina* (Buenos Aires) 58:377–385.

Mayer, Alejandro M.S. and Judy A. Spitzer (1994) "Modulation of Superoxide Generation in In Vivo Lipopolysaccharide–Primed Kupffer Cells by Staurosporine, Okadaic Acid, Manoalide, Arachidonic Acid, Genistein and Sodium Orthovandate" *Journal of Pharmacol. Exp. Ther.* 268:238–247.

Mayer, Alejandro M.S., Stephen Oh, Kyle H. Ramsey, Peer B. Jacobson, Keith B. Glaser, Anne M. Romanic (1999) "*Escherichia Coli* Lipopolysaccharide Potentiation And Inhibition Of Rat Neonatal Microglia Superoxide Anion Generation: Correlation With Prior Lactic Dehydrogenase, Nitric Oxide, Tumor Necrosis Factor–α, Thromboxane $B_2$, and Metalloprotease Release" *Shock* 11(3):180–186.

Mayer, Alejandro M.S. Susan Brenic, Rose Stocker and Keith B. Glaser (1995) "Modulation of Superoxide Generation in in Vivo Lipopolysaccharide–Primed Rat Alveolar Macrophages by ... Tyrosine Kinase(s) and Phosphatase(s)" *Journal of Pharmacology and Experimental Therapeutics* 274(1):427–436.

Faulkner, D.J. (1992) *Natural Products Reports* 9:323–364.

Faulkner, D.J. (1987) *Natural Products Reports* 4(5):539–576.

Faulkner, D.J. (1984) *Natural Products Reports* 1:551–598.

Faulkner, D.J. (1986) *Natural Products Reports* 3:1–33.

Faulkner, D.J. (1993) *Natural Products Reports* 10:497–539.

Faulkner, D.J. (1991) *Natural Product Reports* 8:97147.

Faulkner, D.J. (1990) *Natural Product Reports* 7:269–309.

Faulkner, D.J. (1988) *Natural Product Reports* 5:613–663.

Faulkner, D.J. (1995) *Natural Product Reports* 12:223–269.

Faulkner, D.J. (1994) *Natural Product Reports* 11:355–394.

Primary Examiner—Dwayne C. Jones
(74) Attorney, Agent, or Firm—Saliwanchik, Lloyd & Saliwanchik

(57) ABSTRACT

The subject invention pertains to compounds which are useful as anti-inflammatory agents and to compositions containing such compounds as active ingredients. The novel uses of the compounds relate to the anti-neurogenic inflammatory properties of the disclosed compounds. Specifically exemplified herein is the use of manzamines A, B, C, D, E, and F, and their salts, analogs, and derivatives.

14 Claims, No Drawings

ANTI-INFLAMMATORY USES OF MANZAMINES

CROSS-REFERENCE TO A RELATED APPLICATION

This application claims priority from provisional applications U.S. Ser. No. 60/125,903, filed Mar. 24, 1999 and U.S. Ser. No. 60/164,294, filed Nov. 8, 1999.

The subject invention was made with government support under a research project supported by NOAA/National Sea Grant College Program Grant No. NA66RG0477 Project R/MP-73. The government has certain rights in this invention.

BACKGROUND OF THE INVENTION

The prevention and control of inflammation is often of great importance for the treatment of humans and animals. Much research has been devoted to development of compounds having anti-inflammatory properties. Certain methods and chemical compositions have been developed which aid in inhibiting or controlling inflammation, but additional anti-inflammatory methods and compositions are needed.

Neuroinflammatory conditions are complex and poorly understood disease processes which are hypothesized to involve microglia (BMΦ) (Mallat, M. [1994] *J. Leukoc. Biol.* 56:416–422). BMΦ are mononuclear-phagocytes which become activated in a number of inflammatory conditions, such as neurogenic inflammation, meningitis, septic shock, Down's syndrome, postischemic brain injury, HIV encephalopathy, Parkinson's disease, Alzheimer's disease, amyotrophic lateral sclerosis and multiple sclerosis (Mayer, A. M. [1988 ] *Medicina*. (*B. Aires.*) 58:377–385), acquiring a macrophage-like phenotype and become cytotoxic to brain cells by releasing mediators, i.e., proteolytic enzymes, reactive oxygen intermediates, eicosanoids and cytokines (Mayer et al. [1999] *Shock* 11(3):180–186). Present therapies for these and other inflammatory conditions are based on steroids and nonsteroidal anti-inflammatory compositions which are usually associated with a high incidence of unsatisfactory toxicity and poor efficacy (Faden, A. I. and S. Salzman [1992 ] *Trend in Pharmacological* Sciences 13:29–35).

It has been found that some natural products and organisms are potential sources for chemical molecules having useful biological activity of great diversity. Marine sponges have proved to be such a source, and a number of publications have issued disclosing organic compounds derived from marine sponges. Such publications include Scheuer, P. J. Ed. [1978–1983] *Marine Natural Products, Chemical and Biological Perspectives*, Academic Press, New York; Faulkner, D. [1995–] *J. Nat. Prod. Rep.* 12:223–269; [1994] 11:355–394; [1993] 10:497–539; [1992] 9:323–364; [1991] 8:97–147; [1990] 7:269–309; [1988] 5:613–663; [1987 ] 4:539–576; [1986] 3:1–33; [1984] $O_2^-$1:551–598.

It has been suggested (Glaser, K. B., R. S. Jacobs [1987] *Biochem.* Pharmacol. 36:2079–2086) that manoalide, and other marine natural products have the potential to modulate leukocyte eicosanoid (Mayer, A. M. S., S. Oh, K. H. Ramsey et al. [1999] *Shock* 11(3):180–186) and $O_2^-$ and thromboxane $B_2$ ($TXB_2$) in BMΦ.

Certain cyclic alkaloid compositions, e.g., manzamines A–F derived from extracts of the marine sponge Haliclona sp., have been found to possess useful antitumor activity. These compounds have been described in, for example, U.S. Pat. Nos. 4,895,854; 4,895,853; and 4,895,852. Manzamines A–F have the following structures:

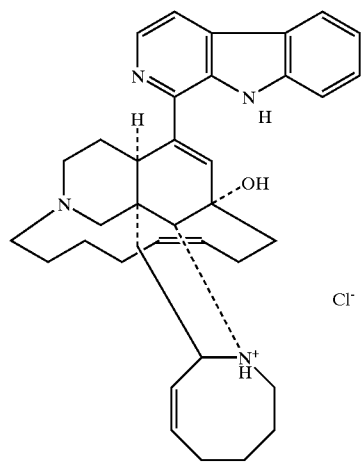

(A)

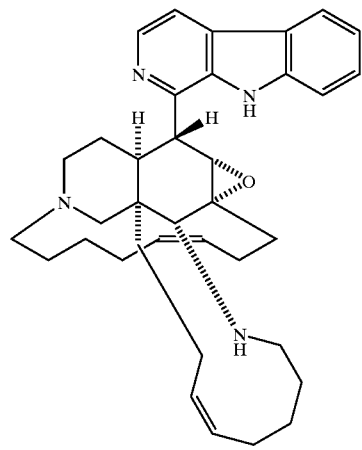

(B)

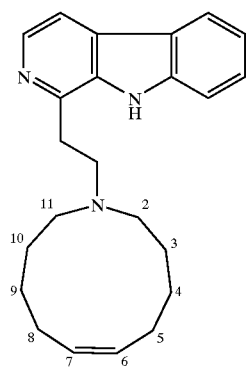

(C)

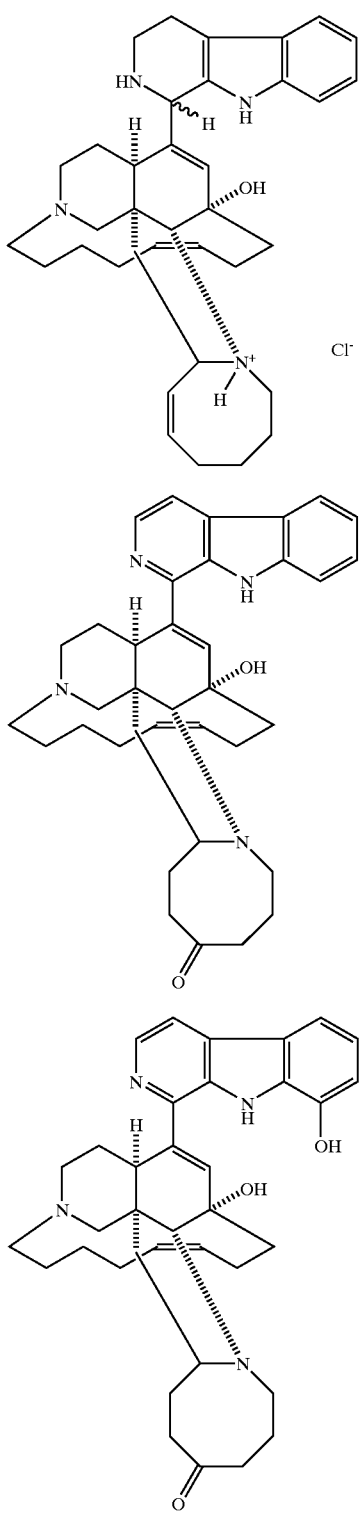

(D)

(E)

(F)

These compounds have not previously been reported to play any role in inflammatory processes.

BRIEF SUMMARY OF THE INVENTION

The objects of the present invention are accomplished by the provision of anti-inflammatory manzamine compounds. Specifically exemplified herein are manzanines A–F. The subject invention further concerns the use of various derivatives and analogs of these compounds. Advantageously, these compounds have been found to possess anti-antigen driven, immune mediated inflammation and anti-neurogenic inflammation activity. Manzamine A has been found to be particularly effective because of its potent anti-inflammatory activity and low toxicity.

As described herein, the invention also comprises pharmaceutical compositions, e.g. anti-inflammatory compositions, containing as an active ingredient an effective amount of one or more compounds described herein and a non-toxic, pharmaceutically acceptable carrier or diluent. The pharmaceutical compositions of the subject invention can further comprise other active compounds. Such other active compounds include, but are not limited to, other anti-inflammatory compounds for example, steroidal compounds, including hydrocortisone and the like; or non-steroidal anti-inflammatories, including acetylsalicylic acid (aspirin), ibuprofen, acetaminophen, indomethacin, and the like. The second active ingredient can include antiviral, antibacterial, antifungal or other antimicrobial compounds or antitumor compounds as well.

As described herein, the invention further comprises processes for the production of compounds and compositions of the invention and novel methods of use thereof, e.g. methods of inhibiting an inflammatory response in a human or animal.

In accordance with the invention, methods for inhibiting inflammation comprise administering to a human or animal in need of such treatment an effective amount of the pharmaceutical compositions described herein.

DETAILED DISCLOSURE OF THE INVENTION

The subject invention pertains to novel uses as anti-inflammatory agents of manzamine compounds and compositions comprising the manzamine compounds. Surprisingly, the manzamine compounds of the subject invention can be highly effective in inhibiting antigen driven, immune-mediated inflammation and neurogenic inflammation activity.

In one embodiment, the subject invention pertains to the use of compounds having the following General Structure (I):

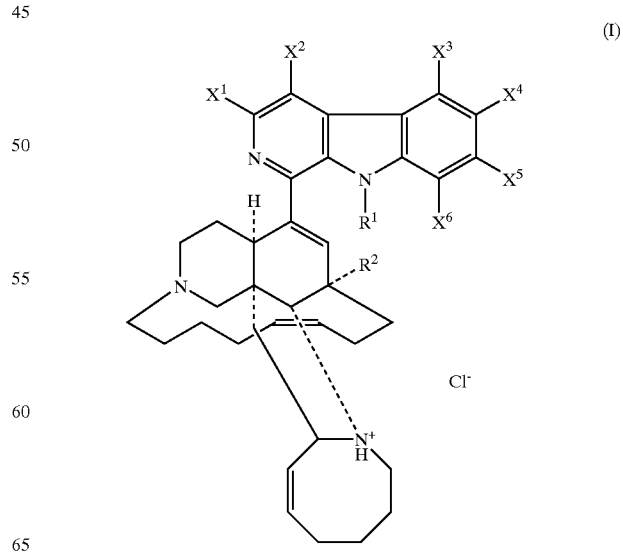

wherein $X^1$, $X^2$, $X^3$, $X^4$, $X^5$, and $X^6$ are, independently, a hydrogen, halogen, hydroxy, lower alkoxy, lower acyloxy, or lower mono or dialkyl amino group; $R^1$ is hydrogen, lower alkyl, or lower acyl group; $R^2$ is hydrogen, hydroxy, lower alkoxy, or lower acyloxy group.

In a preferred embodiment of the invention, the invention pertains to anti-inflammatory compositions comprising manzamine A having the following structure:

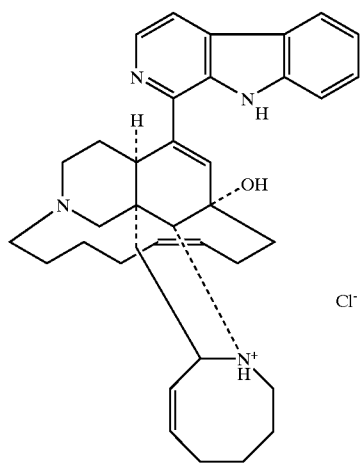

(A)

Further embodiments of the subject invention pertain to the anti-inflammatory use of compounds having General Structures (II)–(IV):

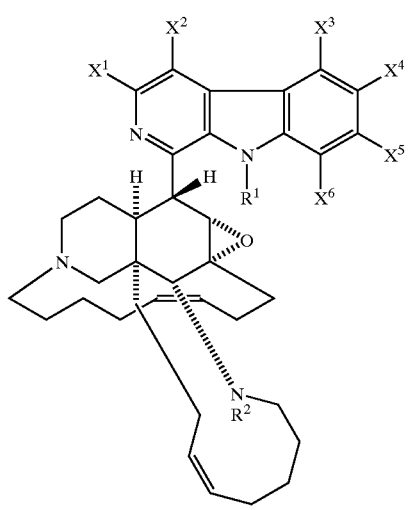

(II)

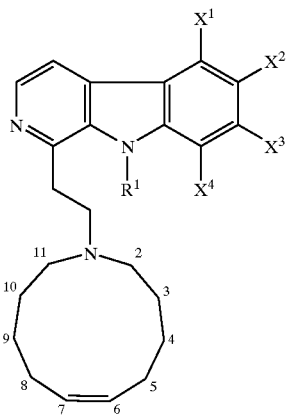

(III)

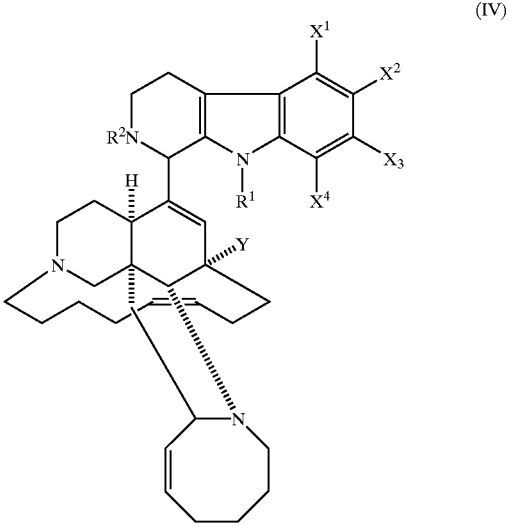

(IV)

wherein $X^1$, $X^2$, $X^3$, $X^4$, $X^5$, and $X^6$ are the same or different and are a hydrogen, halogen, hydroxyl, lower alkoxy, lower acyloxy, thiol, lower alkylthiol, nitro, amino, lower alkylsulfonyl, aminosulfonyl, hydroxy sulfonyl (—SO$_3$H), lower acylamino, lower alkyl, or lower monoalkyl- or dialkyl-amino group; $R^1$ and $R^2$ are the same or different and are a hydrogen, lower alkyl, or lower acyl group; and Y is a hydrogen, hydroxyl, lower alkoxy, or lower acyloxy group.

In more specific embodiments of the invention, the invention comprises the anti-inflammatory use of the compounds designated as manzamine B, C, or D of the formulae:

(B)

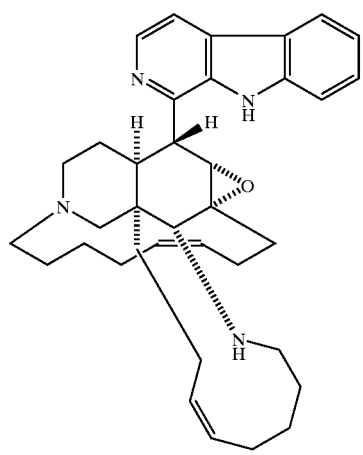

(C)

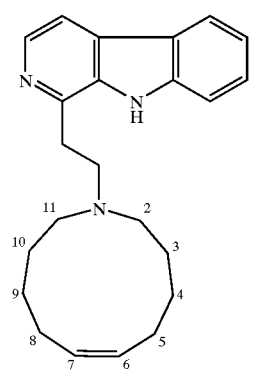

(D)

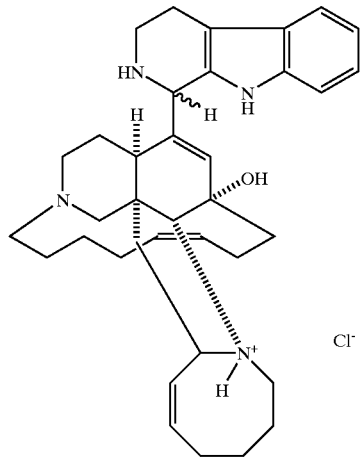

Further embodiments of the subject invention utilize General Structure V:

(V)

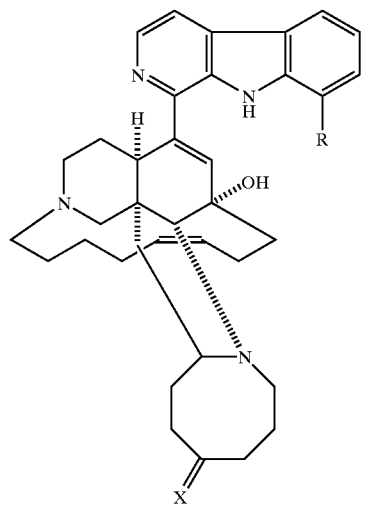

wherein R is a hydrogen, halogen, hydroxy, or lower acyloxy group; and X is a double bonded oxygen, or is the same or different and is any two of a hydrogen, hydroxy, lower alkyl, lower alkoxy, or lower acyloxy group wherein said lower alkyl, alkoxy, or acyloxy groups have preferably, from 1 to 5 carbon atoms.

In a specific embodiment, the subject invention concerns manzamines E and F which have the following structures:

(E)

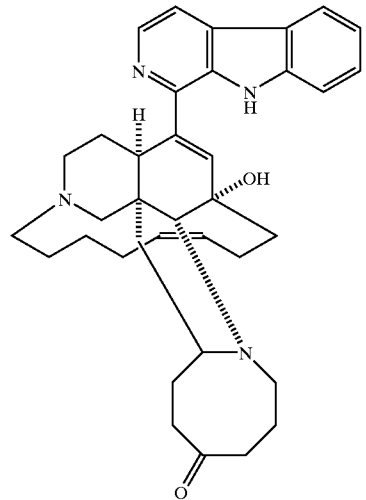

(F)

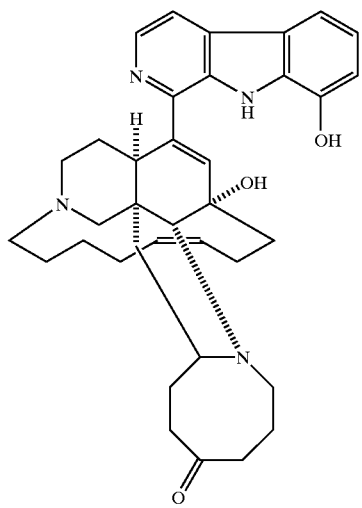

In other embodiments of the invention, the double bonds in the composition of General Structures (I)–(V) are partially or fully reduced. In further embodiments of the invention, the composition is a mineral acid (e.g., HCl, $H_2SO_4$, $H_3PO_4$, $HNO_3$, etc.) or organic salt of compositions according to the General Structures.

Methods for obtaining these compounds are described in, for example, U.S. Pat. Nos. 4,895,852; 4,895,853; and 4,895,854, which are herein incorporated in their entirety by reference thereto.

Skilled chemists having the benefit of the instant disclosure, can readily use procedures to prepare the subject compounds. In carrying out such operations, suitable filtration, chromatographic and other purification techniques can be used. These techniques could include, for example, reversed phase (RPLC), column, vacuum flash, medium pressure (MPLC) and high performance liquid chromatography (HPLC) with a suitable column such as silica gel, Sephadex LH-20, ammonia-treated silica gel, bonded phase RP-18, RP-8 and amino columns. Such columns are eluted with suitable solvents such as heptane, ethyl acetate, methylene chloride, methanol, isopropanol, acetonitrile water, trifluoroacetic acid (TFA) and various combinations thereof.

A novel use for the described compounds and compositions is their administration to an animal or human as an agent in the control of an inflammatory response. The discovery that the subject compounds have inhibitory activity against immune-mediated inflammation and neurogenic inflammation is particularly unexpected and advantageous. Specifically, neurogenic inflammation can be evoked by neuropeptides, such as substance P (SP), calcitonin gene-related peptide (CGRP), vasoactive intestinal peptide (VIP), and neurokinin A (NKA), released from primary afferent C-fiber nerve terminals and histamine, secondarily released from mast cells(Dray, A., [1992] "Neuro pharmacological mechanisms of capsaicin and related substances" *Biochem Pharm* 44(4):611–15). In addition, it is known that capsaicin (CAP), the active constituent found in cayenne pepper, induces an acute neurogenic inflammatory response when applied topically to skin. CAP is a highly selective pain producing substance that selectively stimulates nociceptive and thermal-sensitive nerve endings in tissues by acting on a specific membrane receptor. The mode of action of capsaicin, therefore, differs significantly from phorbol myristate acetate (PMA)-induced immune-inflammation. By comparison, PMA elicits its pro-inflammatory effects through cellular activation of specific immune cells, such as macrophages and microglia. Consequently, the pain response to PMA develops more slowly than the immediate, but transient, pain response to capsaicin.

For purposes of the subject invention, unless otherwise noted, the terms "inflammation" and "inflammatory response" include any and all reactions including, but not limited to, immune-related responses and/or allergic reactions to a physical, chemical, or biological stimulus. "Anti-immune-mediated" and anti-neurogenic inflammatory activity," as used herein, will be understood by those of ordinary skill in the art to mean biological activity inhibiting or controlling an immune-mediated and/or neurogenic inflammatory response. Inflammation for which the primary activating inflammation is antigen-derived can be due to, for example, bacterial lipopolysaccharide.

Anti-inflammatoryactivity can occur by modes of action which can include, but are not limited to, lipid-mediated inflammatory responses, e.g., (i) suppression of cellular activation of phospholipase A2, either directly (as is known for the anti-inflammatory compound, manoalide) or indirectly (as is known for the anti-inflammatory compound, hydrocortisone); (ii) by inhibiting, or controlling, cyclooxygenation of arachidonic acid, similar to the action of non-steroidal anti-inflammatory drugs; or (iii) by affecting lipooxygenase products of peroxidase reactions to arachidonic acid, or by non-lipid-mediated inflammatory responses, which include inflammatory mediators such as cytokines (e.g. tumor necrosis factor alpha, interleukin 1), reactive oxygen species (e.g. superoxide anion ($O_2^-$), hydrogen peroxide ($H_2O_2$) and nitric oxide (NO), proteases, growth factors, complement and excitatory amino acids.

The compounds and compositions of the subject invention can be used in the treatment of inflammation at sites where the primary activating factor is antigen-derived (e.g. bacterial lipopolysaccharide) or of neurogenic origin. In a particularly preferred embodiment, the compounds of the subject invention are used to treat pathological inflammatory conditions of the brain. In a specific embodiment, these pathological inflammatory conditions involve microglia (BMΦ). Thus, the compounds of the subject invention can be used to treat conditions including, but not limited to, neurogenic. inflammation, meningitis, septic shock, Down's syndrome, postischemic brain injury, HIV encephalopathy, Parkinson's disease, Alzheimer's disease, amyotrophic lateral sclerosis and multiple sclerosis.

The subject compounds and compositions can also be useful in the treatment of chronic pain, migraines, thermal-induced pain, such as sunburn, or other thermal and nociceptive pain, and chronic pain associated with arthritis. Uses can also include other inflammatory conditions that involve a neurogenic pain-producing component, e.g., certain metastatic carcinomas or inflammation of the blood vessels.

The compounds of the subject invention can also be used to treat a variety of skin conditions including, but not limited to, radiation irritation and burns (including UV and ionizing), chemical burns, rhinitis, thermal burns, reddening of the skin, and chemically induced lesions.

The compounds of the subject invention can also be used to treat allergic responses and/or promote wound healing. This can include the use of the compounds in aerosol form for the treatment of acute allergic reactions such as acute asthmatic attack and in the treatment of inflammation of the lung caused by chemical exposure.

The compounds of the subject invention can also be used to treat systemic anaphylactic reactions in animals and man.

The compounds of the subject invention can also be used to treat conjunctivitis, inflammatory gum diseases, inflammatory bowel disease, and nephritis.

The compounds of the subject invention can also be used to treat conditions where brain microglia are involved such as neurogenic inflammation, meningitis, septic shock, Down's syndrome, post ischemic brain injury, HIV encephalopathy, Parkinson's disease, Alzheimer's disease, amyotrophic lateral sclerosis, and multiple sclerosis.

Materials and Methods

Chemicals

LPS B (*E. coli.* 026:B6) from Difco Lab, Detroit, Mich.; cytochrome C type III (from horse heart), superoxide dismutase (from bovine liver), phorbol 12-myristate 13-acetate (PMA) and dimethyl sulfoxide (DMSO) from Sigma Chemical Co., St. Louis, Mo. A stock solution of PMA (10 mM) in DMSO was maintained at −80° C. and diluted prior to use. Dulbecco's modified Eagle medium (DMEM) with high glucose (4.5 mg/l), Hanks' balanced salt solution (HBSS), penicillin (P), streptomycin (S), trypsin (0.25%)-EDTA (1 mM) and trypan blue from GIBCO Laboratories, Life Technologies, Inc., Grand Island, N.Y.; heat-inactivated fetal bovine serum certified (FBS) from Hyclone, Logan, Utah. Stock solutions of Manzamine A, B, C, D, E, and F (10 mM) in DMSO were stored at −80° C. and diluted prior to each experiment.

Isolation and Culture of Rat BMΦ

Briefly to prepare primary BMΦ cultures, cerebral cortices from 1–2-day-old Sprague-Dawley rats (Harlan, Indianapolis, Ind.) were placed in cold DMEM+10% heat-inactivated FBS+120 U/ml P and 12 µg/ml S, meninges carefully removed, brain tissue minced and dissociated with trypsin-EDTA at 37° C. for 3–5 minutes. The mixed glial cell suspension was plated in either 75 or 162 cm² culture flasks with DMEM containing 10% heat-inactivated FBS+ 120 U/ml P and 12 µg/ml S and grown in a humidified 5% $CO_2$ incubator at 37° C. On day 7 of culture, flasks were shaken (90 rpm, 20 min, 37° C.) and media exchanged. On day 14 and every 3–4 days thereafter, BMΦ were detached using an orbital shaker (200 rpm, 2 hours, 37° C., 5% $CO_2$), then centrifuged (450×g, 25 min, 4° C.). The pellet containing BMΦ was resuspended gently with cold DMEM, cell number and viability assessed by trypan blue exclusion. Purified BMΦ obtained by our method averaged>than 95% viability. Microglia were characterized as previously described (Mayer et al., 1999, supra).

Assay for BMΦ $O_2^-$ Generation

BMΦ $O_2^-$ generation was determined by the superoxide dismutase(SOD)-inhibitable reduction of ferricytochromeC (FCC) (Mayer et al., 1999, supra). Briefly, spontaneous $O_2^-$ release from unstimulated BMΦ was measured in the presence of FCC (50 µM) and HBSS with or without SOD (700 units). To determine PMA-stimulated $O_2^-$ release, BMΦ containing wells received FCC, HBSS and PMA [1 µM] with or without SOD which inhibited>95% of FCC reduction. All experimental treatments were run in triplicate and in a final volume of 1 ml. Changes in absorbance of BMΦ supernatants were measured at 550 nm using a Beckman DU-650 Spectrophotometer. Differences in the amount of reduced FCC in the presence or absence of SOD were used to determine BMΦ $O_2^-$ generation by employing the molecular extinction coefficient of $21.0 \times 10^3$ $M^{-1}$ $cm^{-1}$.

LDH Assay

To assess BMΦ viability following incubation with vehicle (DMSO) or the manzamines, lactate dehydrogenase (LDH) release was determined spectrophotometrically as previously described (Mayer et al., 1999, supra).

Assay for BMΦ Thromboxane $B_2$ ($TXB_2$) Generation

Following stimulation with PMA, $TXB_2$ generation in the BMΦ culture supernatants was measured using immunoassays (Cayman Chemical, Ann Arbor, Mich.) as indicated by the manufacturer's protocol (Mayer, et al., 1999,supra).

Statistical Analysis of the Data

Data are expressed as means±S.E.M. of triplicate determinations of the number of experiments indicated in the legend of each figure. Appropriate multiway analysis of variance was performed on all sets of data followed by Dunnett's test.

Following are examples which illustrate procedures for practicing the invention. These examples should not be construed as limiting. All percentages are by weight and all solvent mixture proportions are by volume unless otherwise noted.

EXAMPLE 1

Effect of Manzamines on PMA-Stimulated Release of $O_2^-$ and $TXB_2$ from LPS Activated BMΦ

To establish the effect of Manzamine A, B, C, D, E and F on BMΦ $O_2^-$, $TXB_2$, and LDH generation the following procedure was used:

A. Activation of BMΦ with *E. coli* Lipopolysaccharide (LPS):

(1) $2-5 \times 10^5$ BMΦ were seeded into each well of 24-well flat-bottom culture clusters.

(2) 1 ml of DMEM+10% heat-inactivated FBS+120 U/ml P and 12 µg/ml S were added.

(3) BMΦ were allowed to attach for 2 hours, at 37° C., 5% $CO_2$, and monolayers then washed 3 times with 1 ml warm (37° C.) DMEM+10% heat-inactivated FBS+120 U/ml P and 12 µg/ml S were added.

(4) 1 ml of DMEM+10% heat-inactivated FBS+120 U/ml P and 12 µg/ml S were added.

(5) Then, LPS (0.3 ng/ml final concentration) was added to each well.

(6) BMΦ were then incubated for 17 hours in a humidified 5% $CO_2$ incubator at 37° C.

(7) Thereafter, the media was removed from each tissue culture well and discarded.

(8) BMΦ monolayers were washed 3 times with 1 ml warm (37° C.) HBSS.

B. Effect of Manzamines on PMA-stimulated Release of $O_2^-$ and $TXB_2$ from LPS-activated BMΦ

To study the effect of Manzamines A, B, C, D, E and F on PMA-stimulated release of $O_2$ and $TXB_2$ from BMΦ activated with LPS as described in (A) we proceeded as follows.

(1) Add HBSS, Manzamines A, or B, or C, or D, or E, or F, DMSO and Triton X-100 1% to the tissue culture wells containing LPS-activated BMΦ, as shown in Table 1.

(2) Incubate the tissue culture plates for 20 minutes in a humidified 5% $CO_2$ incubator at 37° C.

(3) Remove the tissue culture plates from the incubator and return to laminar flow hood. Add, FCC, SOD and PMA as indicated in Table 1.

(4) Incubate tissue culture plates for an additional 70 minutes in a humidified 5% $CO_2$ incubator at 37° C.

(5) When incubation is complete, aspirate BMΦ supernates from each well (1 ml), and place in a 1.5 ml microcuvette. Proceed to reach absorbance as indicated above in Assay for BMΦ $O_2^-$ generation.

(6) Once (5) is completed use the same BMΦ supernates to determine both LDH and $TXB_2$ as described above in Assay for BMΦ $TXB_2$ generation and LDH assay.

TABLE 1

A typical experimental protocol to study the Manzamines

| Group | Concentration[1] µM | Well | HBSS[2] µL | PMA[3] µL | FCC[4] µL | TX-100[5] µL | SOD[6] µL | Total volume µL |
|---|---|---|---|---|---|---|---|---|
| Manz[7] | 0.1–10 | 1, 2, 3 | 800 | 100 | 100 | — | — | 1,000 |
| Vehicle[8] | 0.2% | 4, 5, 6 | 800 | 100 | 100 | — | — | 1,000 |
| TX-100 | 0.1% | 7, 8, 9 | 800 | — | 100 | 100 | — | 1,000 |
| SOD | | 10, 11, 12 | 800 | — | 100 | — | 100 | 1,000 |

Notes:
[1]Concentration: final concentration of manzamine, vehicle (DMSO), Triton X-100.
[2]HBSS: Hanks' balanced salt solution.
[3]PMA: stock is 10 µM, final concentration is 1 µM.
[4]FCC: ferricytochrome C stock is 500 µM, final concentration is 50 µM.
[5]TX-100: Triton X-100 stock is 1%, final concentration is 0.1%.
[6]SOD: superoxide dismutase stock is 3500 units/ml, final concentration is 350 units/ml.
[7]Manzamine A, B, C, D, E, or F: 2 µL were added to each 1,000 µL. Concentration range studied varied from 0.1 µM to 10 µM.
[8]DMSO: 2 µL were added to each 1,000 µL, thus final concentration was 0.2%. This amount of DMSO is equivalent to the amount manzamine-treated wells received, since all dilutions of manzamines were done in DMSO.

EXAMPLE 2

The results of the Structure-Activity Relationship study with Manzamines A, B, C, D, E and F are shown in Table 2.

TABLE 2

| Manzamine | $IC_{50}$ $O_2^-$ µM | $IC_{50}$ $TXB_2$ µM | $IC_{50}$ LDH µM |
|---|---|---|---|
| A | 0.1 | <0.1 | >30 |
| B | ±5 | ±3 | ±3 |
| C | ±5 | ±5 | ±5 |
| D | ±0.5 | ±0.3 | ±0.5 |
| E | >10 | 10 | >10 |
| F | >10 | >>10 | >10 |

From the results shown in Table 2, it is clear that manzamine A is particularly advantageous for the following reasons:

(1) Manzamine A inhibits $O_2^-$ generation with an $IC_{50}$ of 0.1 µM, which is much lower than that for Manzamine B, C, D, E and F. In other words, Manzamine A, is a more potent inhibitor of $O_2^-$ than Manzamine B, C, D, E and F.

(2) Manzamine A inhibits $TXB_2$ generation with an $IC_{50}$ less than 0.1 µM which is much lower than that of Manzamine B, C, D, E and F. In other words, Manzamine A is a more potent inhibitor of $TXB_2$ than Manzamine B, C, D, E and F.

(3) Manzamine A causes release of LDH with an $IC_{50}$ greater than 30 µM, which is much higher than that of Manzamine B, C, D, E and F. In other words, Manzamine A is less toxic than Manzamine B, C, D, E and F.

EXAMPLE 3
Formulation and Administration

The compounds of the invention are useful for various non-therapeutic and therapeutic purposes. It is apparent from the testing that the compounds of the invention are effective for anti-inflammatory uses.

Therapeutic application of the new compounds and compositions containing them can be contemplated to be accomplished by any suitable therapeutic method and technique presently or prospectively known to those skilled in the art. Further the compounds of the invention have use as starting material for intermediates for the preparation of other useful compounds and compositions.

In one embodiment, the compounds or compositions of the subject invention are administered in a lotion or other cosmetic preparation. This administration is done directly to the skin where anti-inflammatory activity is desired.

The dosage administration to a host in the above indications will be dependent upon the identity of the infection, the type of host involved, its age, weight, health, kind of concurrent treatment, if any, frequency of treatment and therapeutic ration.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the manzamine compounds as a first active ingredient plus a second active ingredient comprising an anti-inflammatory compound known in the art. Such known anti-inflammatory drugs include, but are not limited to, the steroidal anti-inflammatory drugs and the non-steroidal anti-inflammatory drugs (NSAIDs).

In accordance with this invention, pharmaceutically effective amounts of a known anti-inflammatory agent and the manzamine compounds are administered sequentially or concurrently to the patient. The most effective mode of administration and dosage regimen of manzamine compounds and anti-inflammatory agent will depend upon the type of condition to be treated, the severity and course of that condition, previous therapy, the patient's health status, and response to manzamines and the judgment of the treating physician. Manzamine compositions may be administered to the patient at one time or over a series of treatments.

Preferably, the manzamine composition, and any second anti-inflammatory agent are administered sequentially to the patient, with the anti-inflammatory agent being administered before, after, or both before and after treatment with the manzamine compound. Sequential administration involves treatment with the anti-inflammatory agent at least on the same day (within 24 hours) of treatment with manzamine and may involve continued treatment with the anti-inflammatory agent on days that the manzamine is not administered. Conventional modes of administration and standard dosage regimens of anti-inflammatory agents may be used (see Gilman, A. G. et. al. [eds] *The Pharmacological Basis of Therapeutics*, pp.697–713, 1482, 1489–1491 [1980]; Physicians Desk Reference, 1985 Edition). For example, indomethacin can be administered orally at a dosage of about 25–50 mg, three times a day. Higher doses can also be used. Alternatively, aspirin (about 1500–2000 mg/day), ibuprofen (about 1200–3200 mg/day), or conventional therapeutic doses of other anti-inflammatory agents can be used. Dosages of anti-inflammatory agents can be titrated to the individual patient.

According to one embodiment of this invention, the patient may receive concurrent treatments with the anti-inflammatory agents and compositions comprising manzamines. For example, local intralesional, or intravenous injection of manzamines is preferred (see Gilman et. al. supra at pp. 1290–91). The anti-inflammatory agent should preferably be administered by subcutaneous injection, subcutaneous slow release implant, or orally.

Alternatively, the patient can receive a composition comprising a combination of one or more manzamine compounds and an anti-inflammatory agent according to conventional modes of administration of agents which exhibit antibacterial, anticancer, antitumor or anti-inflammatory activity. These include, for example, parenteral, subcutaneous, intravenous, or intralesional routes of administration.

The compounds used in these therapies can also be in a variety of forms. These include for example, solid, semi-solid and liquid dosage forms, such as tablets, pills, powders, liquid solutions or suspensions, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch and equivalent carriers and diluents. While effective amounts may vary, as conditions in which compositions are used vary, a minimal dosage required for anti-inflammatory activity is generally between 0.01 and 100 µg of the compound. To provide for the administration of such dosages for the desired therapeutic treatment, new pharmaceutical compositions of the invention will advantageously comprise between about 0.1% and 45%, and especially, 1 and 15% by weight of the total of one or more of the new compounds based on the weight of the total composition including carrier or diluent.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 20 mg/kg; and aerosol, 0.01 to about 20 mg/kg of animal (body) weight.

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of treating inflammation in a human or animal, wherein said method comprises administering to said human or animal an effective amount of a compound, or a salt thereof, wherein said compound has a formula selected from the group consisting of:

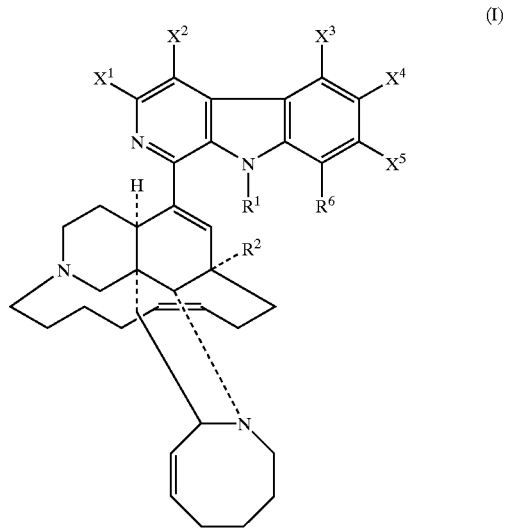

(I)

wherein $X^1$, $X^2$, $X^3$, $X^4$, $X^5$, and $X^6$ are, independently, a hydrogen, halogen, hydroxy, lower alkoxy, lower acyloxy, or lower mono or dialkyl amino group; $R^1$ is a hydrogen, lower alkyl or lower acyl group; $R^2$ is a hydrogen, hydroxy, lower alkoxy or lower acyloxy group;

acyloxy, thiol, lower alkylthiol, nitro, amino, lower alkylsulfonyl, aminosulfonyl, hydroxy sulfonyl (—SO$_3$H), lower acylamino, lower alkyl, or lower monoalkyl- or dialkyl-amino group; R$^1$ and R$^2$ are the same or different and are a hydrogen, lower alkyl, or lower acyl group; and Y is a hydrogen, hydroxyl, lower alkoxy, or lower acyloxy group wherein R is a hydrogen, halogen, hydroxy, or lower acyloxy group; and X is a double bonded oxygen, or is the same or different and is any two of a hydrogen, hydroxy, lower alkyl, lower alkoxy, or lower acyloxy group wherein said lower alkyl, alkoxy, or acyloxy groups have from 1 to about 5 carbon atoms.

2. The method, according to claim 1, wherein said compound has the following structure:

wherein X$^1$, X$^2$, X$^3$, X$^4$, X$^5$, and X$^6$ are the same or different and are a hydrogen, halogen, hydroxyl, lower alkoxy, lower wherein $X^1$, $X^2$, $X^3$, $X^4$, $X^5$, and $X^6$ are a hydrogen, halogen, hydroxy, lower alkoxy, lower acyloxy, or lower mono or dialkyl amino group; $R^1$ is hydrogen, lower alkyl, or lower acyl group; $R^2$ is hydrogen, hydroxy, lower alkoxy, or lower acyloxy group.

3. The method, according to claim 2, wherein said compound has the following structure:

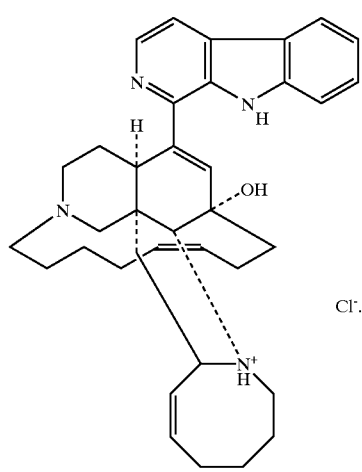

(A)

4. The method, according to claim 1, wherein said compound has the following structure:

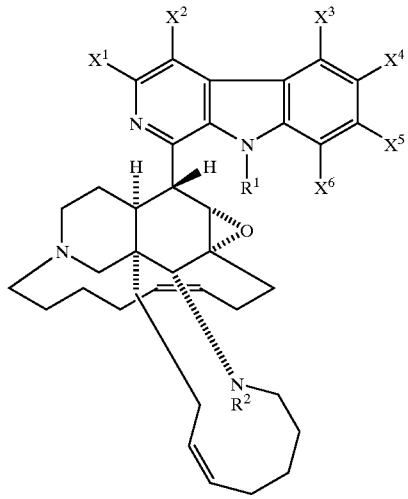

(II)

wherein $X^1$, $X^2$, $X^3$, $X^4$, $X^5$, and $X^6$ are the same or different and are a hydrogen, halogen, hydroxyl, lower alkoxy, lower acyloxy, thiol, lower alkylthiol, nitro, amino, lower alkylsulfonyl, aminosulfonyl, hydroxy sulfonyl (—SO$_3$H), lower acylamino, lower alkyl, or lower monoalkyl- or dialkyl-amino group; $R^1$ and $R^2$ are the same or different and are a hydrogen, lower alkyl, or lower acyl group; and Y is a hydrogen, hydroxyl, lower alkoxy, or lower acyloxy group.

5. The method, according to claim 4, wherein said compounds has the following structure:

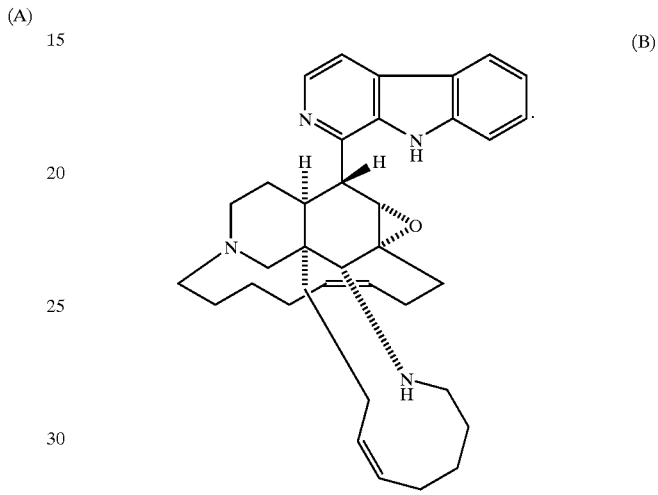

(B)

6. The method, according to claim 1, wherein said compound has the following structure:

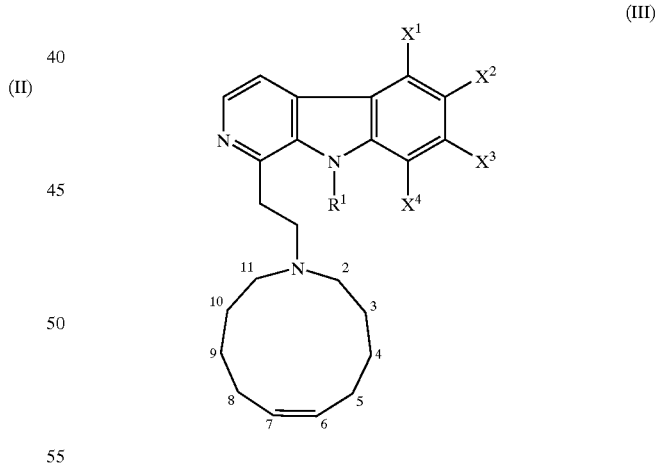

(III)

wherein $X^1$, $X^2$, $X^3$, and $X^4$ are the same or different and are a hydrogen, halogen, hydroxyl, lower alkoxy, lower acyloxy, thiol, lower alkylthiol, nitro, amino, lower alkylsulfonyl, aminosulfonyl, hydroxy sulfonyl (—SO$_3$H), lower acylamino, lower alkyl, or lower monoalkyl- or dialkyl-amino group; and $R^1$ is a hydrogen, lower alkyl, or lower acyl group.

7. The method, according to claim 6, wherein said compound has the following structure:

(C)

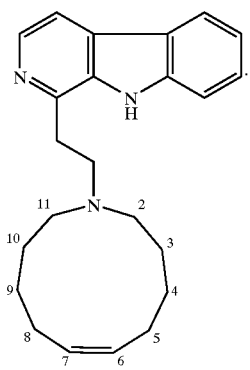

8. The method, according to claim 1, wherein said compound has the following structure:

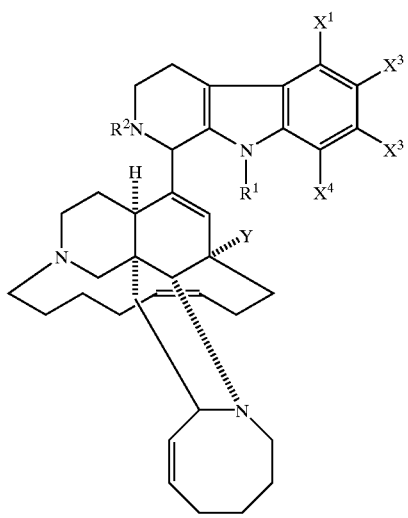

(IV)

wherein $X^1$, $X^2$, $X^3$, and $X^4$ are the same or different and are a hydrogen, halogen, hydroxyl, lower alkoxy, lower acyloxy, thiol, lower alkylthiol, nitro, amino, lower alkylsulfonyl, aminosulfonyl, hydroxy sulfonyl (—SO$_3$H), lower acylamino, lower alkyl, or lower monoalkyl- or dialkyl-amino group; $R^1$ and $R^2$ are the same or different and are a hydrogen, lower alkyl, or lower acyl group; and Y is a hydrogen, hydroxyl, lower alkoxy, or lower acyloxy group.

9. The method, according to claim 8, wherein said compound has the following structure:

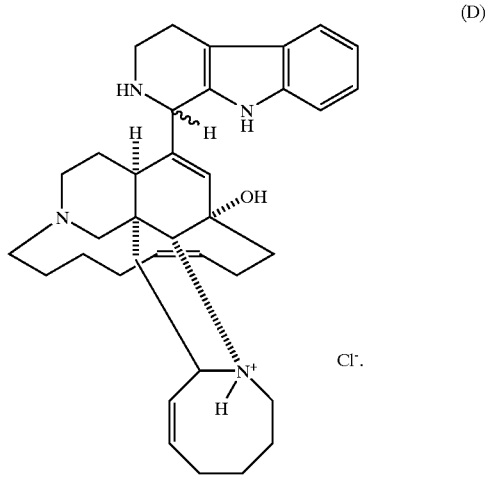

(D)

10. The method, according to claim 1, wherein said compound has the following structure:

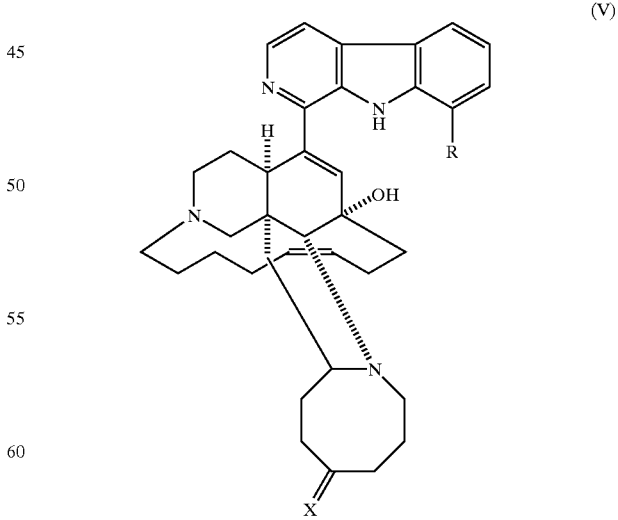

(V)

wherein R is a hydrogen, halogen, hydroxy, or lower acyloxy group; and X is a double bonded oxygen, or is the same or different and is any two of a hydrogen, hydroxy, lower alkyl, lower alkoxy, or lower acyloxy group wherein said lower alkyl, alkoxy, or acyloxy groups have from 1 to about 5 carbon atoms.

11. The method, according to claim 8, wherein said compound has the following structure:

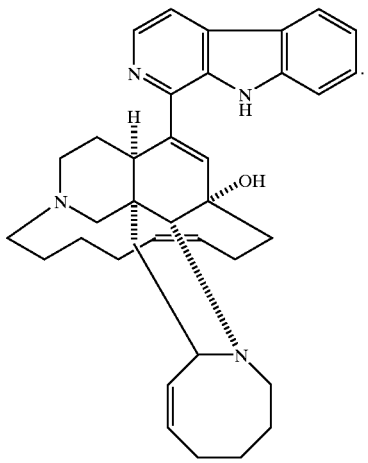

12. The method, according to claim 10, wherein said compound has the following structure:

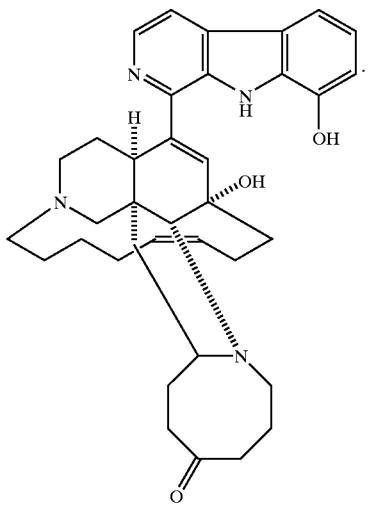

(F)

13. The method, according to claim 1, wherein said method is used to treat inflammation in which the primary activating inflammation is antigen-derived or of neurogenic origin.

14. The method, according to claim 1, wherein said compound is administered as a pharmaceutical composition, said pharmaceutical composition comprising one or more compounds of claim 1 and an acceptable pharmaceutical carrier.

* * * * *

UNITED STATES PATENT AND TRADEMARK OFFICE
CERTIFICATE OF CORRECTION

PATENT NO. : 6,387,916 B1
DATED : May 14, 2002
INVENTOR(S) : Alejandro Mayer et al.

It is certified that error appears in the above-identified patent and that said Letters Patent is hereby corrected as shown below:

Column 1,
Line 51, "[1995-]" should read -- [1995] --.

Column 10,
Line 14, "Anti-inflammatoryactivity" should read -- Anti-inflammatory activity --.

Column 11,
Line 63, "means±S.E.M." should read -- means ± S.E.M. --.

Column 16,
Figure I, line 46, "$R^6$" should read -- $X^6$ --.

Column 21,
Figure IV, line 31, ""$X^3$" should read -- $X^2$ --.

Signed and Sealed this

Fourth Day of February, 2003

JAMES E. ROGAN
*Director of the United States Patent and Trademark Office*